United States Patent [19]
Frankowiak et al.

[11] Patent Number: 5,399,149
[45] Date of Patent: Mar. 21, 1995

[54] KNEE HINGE WITH SELECTIVELY LIMITED MOTION

[76] Inventors: Ray M. Frankowiak, 120 Christy Crt., Athens, Ga. 30605; Gunter R. Sprang, 74 Birch Rill Dr., Alphareta, Ga. 30202

[21] Appl. No.: 102,355

[22] Filed: Aug. 5, 1993

[51] Int. Cl.⁶ .............................................. A61F 5/00
[52] U.S. Cl. ...................................... 602/16; 602/26; 403/106; 403/104; 403/325; 403/322; 16/326
[58] Field of Search .................... 602/5, 16, 26, 20, 23; 128/870, 882; 16/326; 403/107, 106, 104, 103, 97, 98, 325, 322

[56] References Cited

U.S. PATENT DOCUMENTS

| | | | |
|---|---|---|---|
| 2,413,634 | 12/1946 | Kolarik | 602/16 |
| 2,591,373 | 4/1952 | Petruch | 602/26 |
| 2,812,961 | 11/1957 | Brown et al. | 403/95 X |
| 3,552,786 | 1/1971 | Schmid | 403/158 X |
| 4,577,986 | 3/1986 | Wang | 403/95 X |
| 4,605,227 | 8/1986 | Hurd et al. | 403/104 X |
| 5,025,782 | 6/1991 | Salerno | 602/26 X |
| 5,031,606 | 7/1991 | Ring, Sr. | 602/26 X |

FOREIGN PATENT DOCUMENTS 2161388  1/1986  United Kingdom ............... 602/16

Primary Examiner—Richard J. Apley
Assistant Examiner—Linda C. M. Dvorak
Attorney, Agent, or Firm—Hugh E. Smith

[57] ABSTRACT

A knee hinge with selectively limited motion which optionally limits an available flexion range of a user's knee to approximately 24 degrees so that a user will not fall should the user buckle at the knees. The hinge may be released to provide for a greater range of knee flexion which will allow a user to sit down in a conventional manner. The approximately 24 degree limit of the flexion range is automatically re-engaged when the user's knee is straightened. The hinge provides a spring mechanism for assisting weak knee muscles. The hinge also allows a small degree of knee hyperextension for the purpose of allowing the user to assume and maintain a safe standing position.

4 Claims, 6 Drawing Sheets

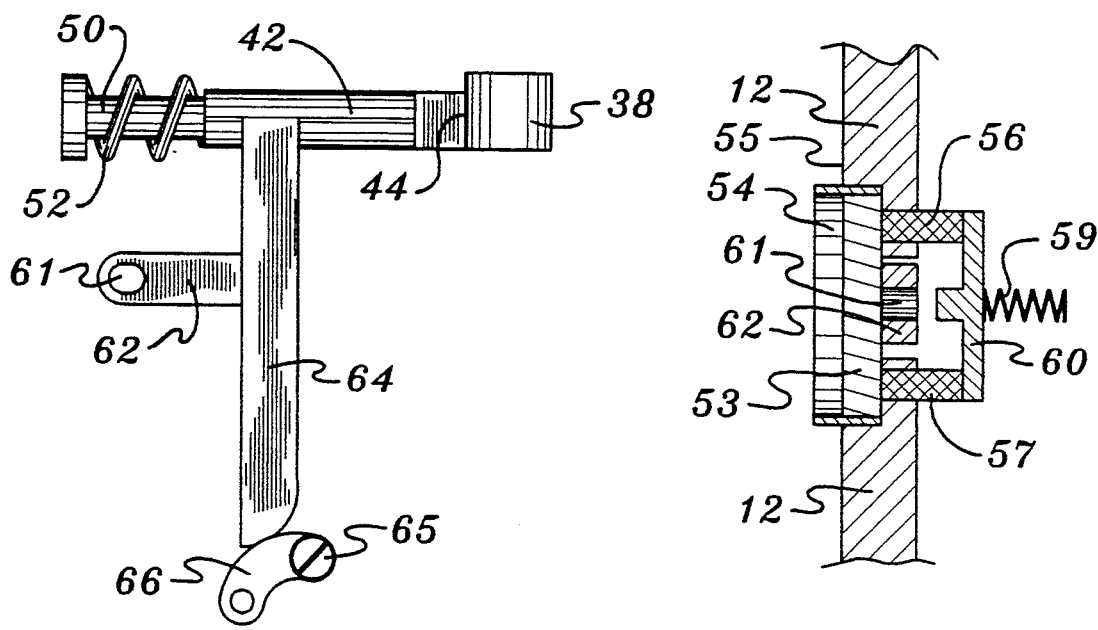
FIG. 7
FIG. 9
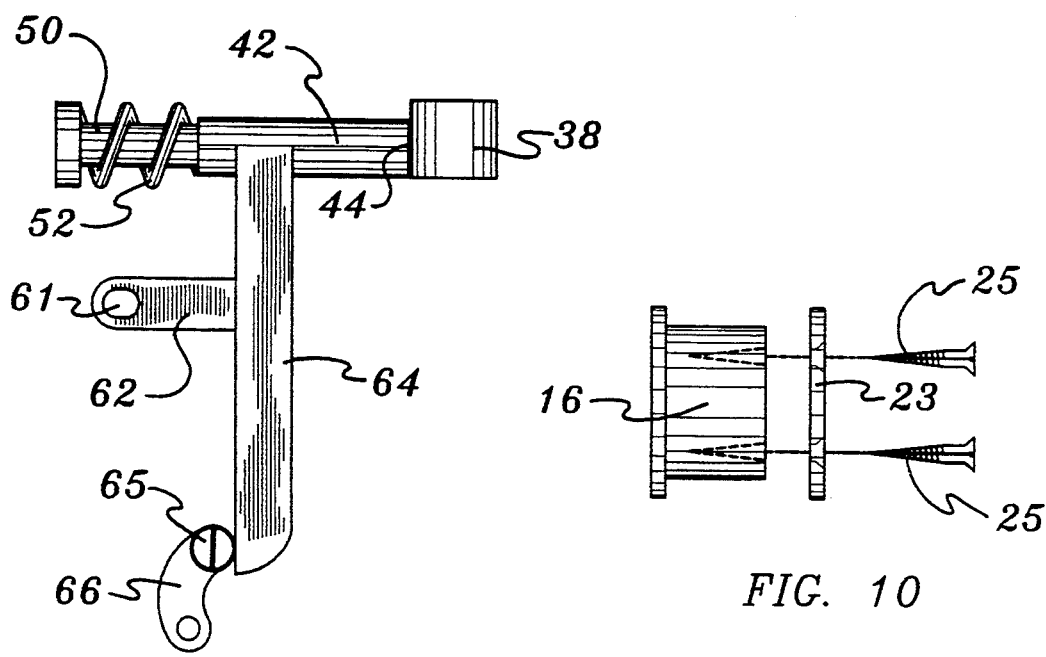
FIG. 8
FIG. 10

KNEE HINGE WITH SELECTIVELY LIMITED MOTION

BACKGROUND OF THE INVENTION

1. Field of the Invention

The present invention relates to hinges and more particularly pertains to knee hinges which may be utilized on a knee brace and the like.

2. Description of the Prior Art

Knee braces are often utilized to support a user's knee when damage, disease, surgery, or the like has caused the knee to become weakened and unstable. Commonly, a knee brace is utilized both to provide extra support to the knee and to protect the knee from further injury. Priorly, knee braces of a variety of different forms have been employed to substantially support and/or strengthen a user's knee. A common method of creating additional support has been achieved by simply wrapping a material, such as an elasticized band, around a user's knee joint. Such a wrapping provides additional support to a user's knee, but only to a small degree.

Because of the modest support provided by this method, knee braces including hinges have been utilized to provide greater support to a user's knee. Substantially all of the prior art knee braces utilize similar leg supports, but differ both in their structure and in their use by subtle differences in the hinges that result in distinctive operating characteristics.

For example, a knee brace hinge is illustrated in U.S. Pat. No. 5,074,290 which utilizes a floating pivot point that allows the hinge to follow a natural motion of a user's knee.

Another knee brace hinge is described in U.S. Pat. No. 4,911,709 which utilizes a four bar linkage geometry that permits the available degree of knee flexion to be approximately 143 degrees.

U.S. Pat. No. 5,063,916 discloses a knee brace having a freecentric hinge that includes a locking mechanism to prevent hyperextension of a user's knee.

While all of the aforementioned patents serve to provide additional support and protection to a user's knee, none of the above patents discloses a knee hinge that will limit the range of knee flexion so as to reduce the danger presented should a user's knee buckle. A knee flexion of approximately 24 degrees will allow a user to walk or run normally and limiting the range of knee flexion to this amount will prevent a patient from falling if the user's knee should buckle. Therefore, it is desirable for a knee hinge to limit the available range of knee flexion to approximately 24 degrees.

It is also desirable for a knee hinge to incorporate other features as well. A knee hinge should selectively allow a full knee flexion range to permit a user to assume a conventional seating position and it should also allow a small amount of knee hyperextension for the purpose of allowing the user to assume and maintain a safe standing position. In addition, a knee hinge should be operable to selectively assist a user's knee in returning to a straightened position during walking and similar activities to compensate for damaged or weak supporting knee muscles.

Therefore, it can be appreciated that there exists a continuing need for a new knee hinge with selectively limited motion which can be utilized both to limit the range of knee flexion so as to reduce the danger from a user's knee buckling and to selectively allow a full knee flexion range which will permit a user to assume a conventional seating position. In this regard, the present invention substantially fulfills this need.

SUMMARY OF THE INVENTION

In view of the foregoing disadvantages inherent in the known types of knee brace hinges now present in the prior art, the present invention provides a new knee hinge with selectively limited motion wherein the same can be utilized both to limit the range of knee flexion so as to reduce the danger from a user's knee buckling and to selectively allow a full knee flexion range which will permit a user to assume a conventional seating position. As such, the general purpose of the present invention, which will be described subsequently in greater detail, is to provide a new knee hinge with selectively limited motion which has many of the advantages of the knee brace hinges mentioned heretofore and many novel features which result in a knee hinge with selectively limited motion that is not anticipated, rendered obvious, suggested, or even implied by any of the prior art knee brace hinges, either alone or in any combination thereof.

To attain this, the present invention essentially comprises a knee hinge with selectively limited motion which optionally limits an available flexion range of a user's knee to approximately 24 degrees so that a user will not fall should the user buckle at the knees. The hinge may also be released to provide for up to approximately 102 degrees of knee flexion which will allow a user to sit down in a conventional manner. The approximately 24 degree limit of the flexion range is automatically re-engaged when the user's knee is straightened. The hinge further provides a substantially J-shaped motion that follows a user's natural knee motion and it further provides a spring mechanism for assisting weak knee muscles. The hinge also allows up to five degrees of knee hyperextension for the purpose of allowing the user to assume and maintain a safe standing position.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new knee hinge with selectively limited motion apparatus which has many of the advantages of the knee brace hinges mentioned heretofore and many novel features that result in a knee hinge with selectively limited motion which is not anticipated, rendered obvious, suggested, or even implied by any of the prior art knee brace hinges, either alone or in any combination thereof.

It is another object of the present invention to provide a new knee hinge with selectively limited motion which may be easily and efficiently manufactured and marketed.

It is a further object of the present invention to provide a new knee hinge with selectively limited motion which is of a durable and reliable construction.

An even further object of the present invention is to provide a new knee hinge with selectively limited motion which is susceptible of a low cost of manufacture with regard to both materials and labor, and which accordingly is then susceptible of low prices of sale to the consuming public, thereby making such knee hinges with selectively limited motion economically available to the buying public.

Still yet another object of the present invention is to provide a new knee hinge with selectively limited motion which provides in the apparatuses and methods of the prior art some of the advantages thereof, while simultaneously overcoming some of the disadvantages normally associated therewith.

Still another object of the present invention is to provide a new knee hinge with selectively limited motion which optionally limits an available flexion range of a user's knee to a predetermined degree of knee flexion so that a user will not fall should the user buckle at the knees.

Yet another object of the present invention is to provide a new knee hinge with selectively limited motion which may be released to provide a substantially unrestricted amount of knee flexion, thereby to allow a user to sit in a conventional manner.

Even still another object of the present invention is to provide a new knee hinge with selectively limited motion that provides a spring mechanism for selectively assisting a user's knee muscles.

Even still yet another object of the present invention is to provide a new knee hinge with selectively limited motion that allows a small degree of knee hyperextension for the purpose of allowing the user to assume and maintain a safe standing position.

Even yet another further object of the present invention is to provide a new knee hinge with selectively limited motion that substantially follows a natural motion of a user's knee.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 7 is a side elevation view of a portion of the present invention.

FIG. 8 is a side elevation view of a portion of the invention.

FIG. 9 is a cross section view taken along line 9—9 of FIG. 6.

FIG. 10 is a side elevation view of a further portion of the present invention.

DESCRIPTION OF THE PREFERRED EMBODIMENT

Figures 1, 2:
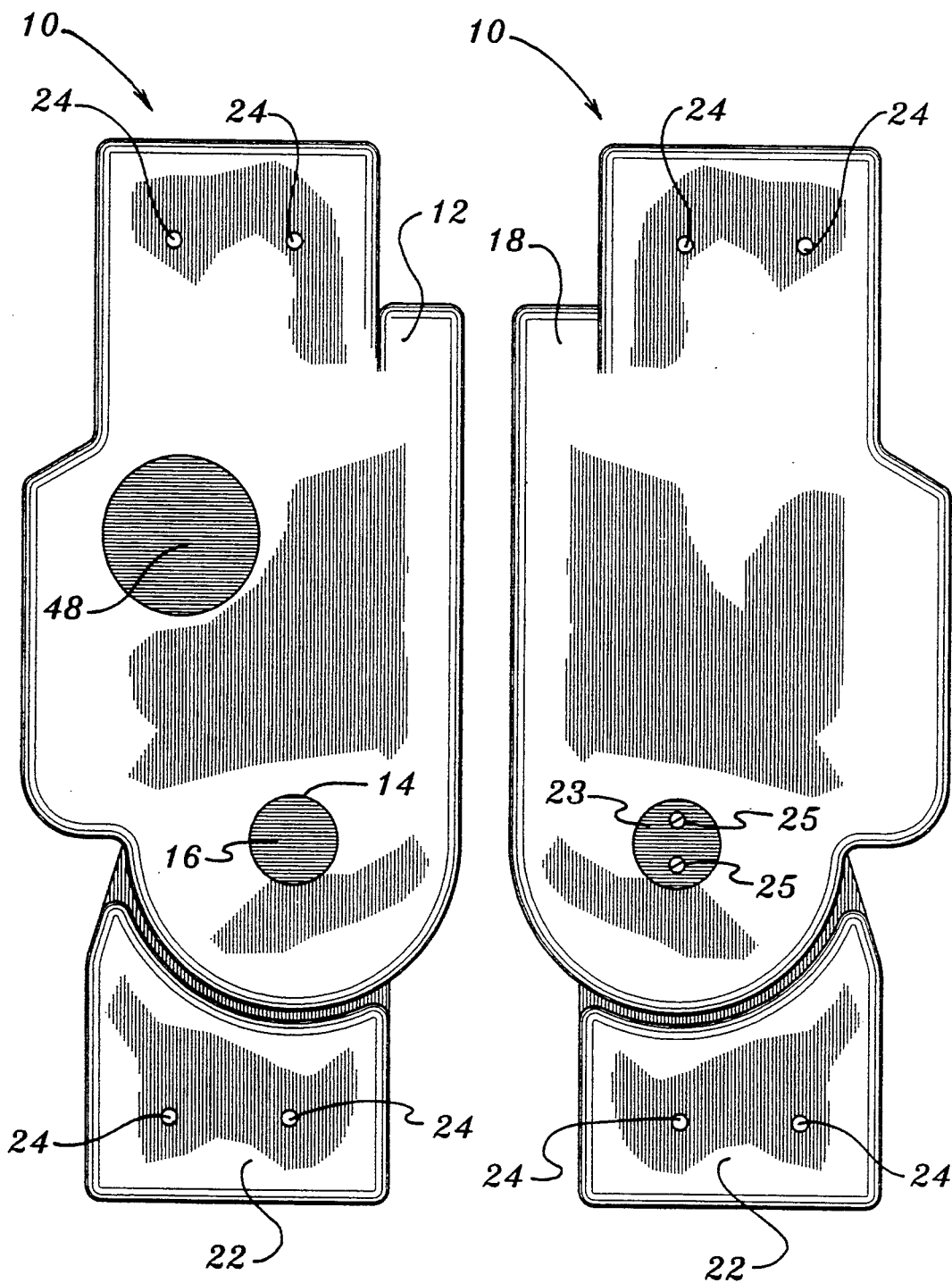
FIG. 1 is a side elevation view of a knee hinge with selectively limited motion comprising the present invention.
FIG. 2 is a side elevation view of the knee hinge of the present invention.
Figure 3:
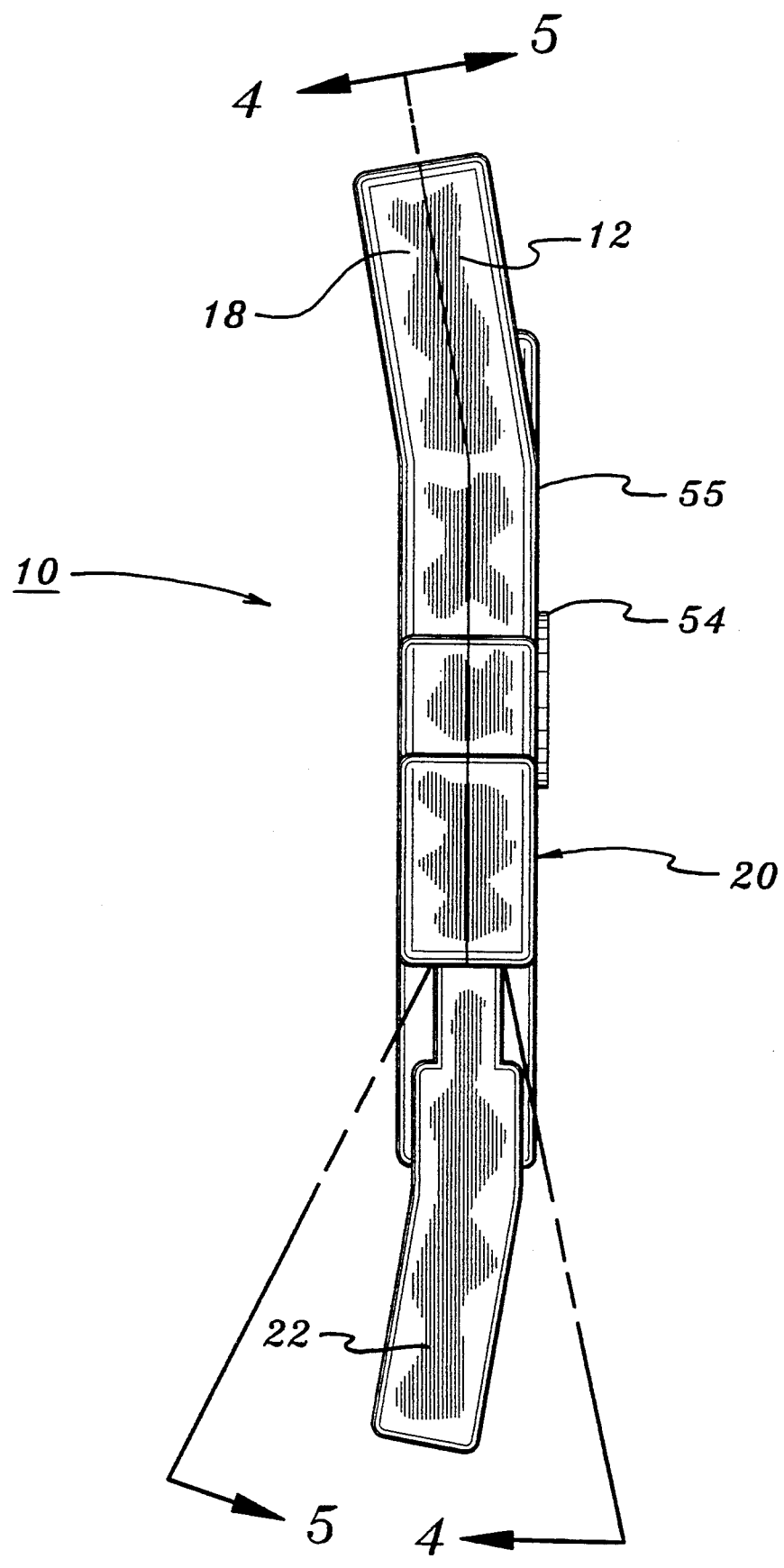
FIG. 3 is a front elevation view of the invention.

With reference now to the drawings, and in particular to FIGS. 1-10 thereof, a new knee hinge with selectively limited motion embodying the principles and concepts of the present invention and generally designated by the reference numeral 10 will be described.

More specifically, it will be noted that the knee hinge with selectively limited motion 10 comprises a left member 12 which is substantially flat in shape and has an aperture 14 which allows a pivot pin 16 to pass therethrough. A right member 18 is formed in a substantially oppositely similar shape as the left member 12 so that the right member may be joined to the left member to form a substantially flat hinge casing assembly 20. The right member 18 also has a correspondingly positioned and unlabeled aperture that allows the pivot pin 16 to pass therethrough. Positioned between both the left member 12 and the right member 18 is a hinge arm 22 that is pivotally supported therebetween by the pivot pin 16 which passes through both an oblong aperture 21 in the hinge arm and the apertures 14, 21 in the left and right members, respectively. The pivot pin 16 is fastened to the hinge casing assembly 20 by a plate 23 which is secured to the pivot pin by a pair of fasteners 25. The plate 23 serves to prevent an axial movement of the pivot pin, thereby restraining it within the hinge casing assembly 20. A plurality of apertures 24 extend through hinge casing assembly 20 for allowing appropriate fasteners (not shown) to secure the hinge 10 to a suitable knee brace. The hinge arm 22 is also similarly equipped with a plurality of apertures 24 that are operable to provide a substantially similar use as well. When installed upon a knee brace, the hinge casing assembly 20 supports an upper portion of the knee brace and the hinge arm 22 supports a lower portion of the knee brace. During operation, the hinge arm 22 pivots about the pivot pin with respect to the hinge casing assembly 20 in a plane substantially parallel to the hinge casing assembly.

A motion that the knee hinge 10 assumes as the hinge arm 22 pivots about the pivot pin 16 is defined by both the oblong aperture 21 of the hinge arm and a guide journal 26. Positioned upon the hinge arm 22 in an eccentric relationship to the oblong aperture 21 is a projection 28 that engages and follows the guide journal 26. The guide journal 26 is integrally formed into the right member 18 and serves to guide the hinge arm 22 into a substantially J-shaped motion as the hinge arm pivots about the pivot pin 16. The guide journal 26 and the oblong aperture 21 are positioned in such a manner so as to provide a knee flexion range of approximately five degrees of knee hyperextension and approximately 102 degrees of knee flexion. The amount of knee hyperextension and knee flexion afforded to the invention 10 is not meant to be limiting in any manner since varying amounts of both knee hyperextension and knee flexion can be incorporated into the knee hinge 10.

During use, the knee hinge 10 limits a range of knee flexion so as to reduce the danger presented should a user's knee buckle. A knee flexion of approximately 24 degrees will allow a user to walk or run and limiting the range of knee flexion to this amount will prevent a patient from falling if the user's knee should buckle. Although a limited knee flexion range of 24 degrees is considered appropriate to prevent a fall from occurring should the user buckle at the knee, it should not be regarded as possibly restricting the breadth of the invention 10 since any conceivable variation in the limited knee flexion range may be incorporated into the knee hinge 10 while still remaining within the spirit and scope of the present invention.

Figure 4:
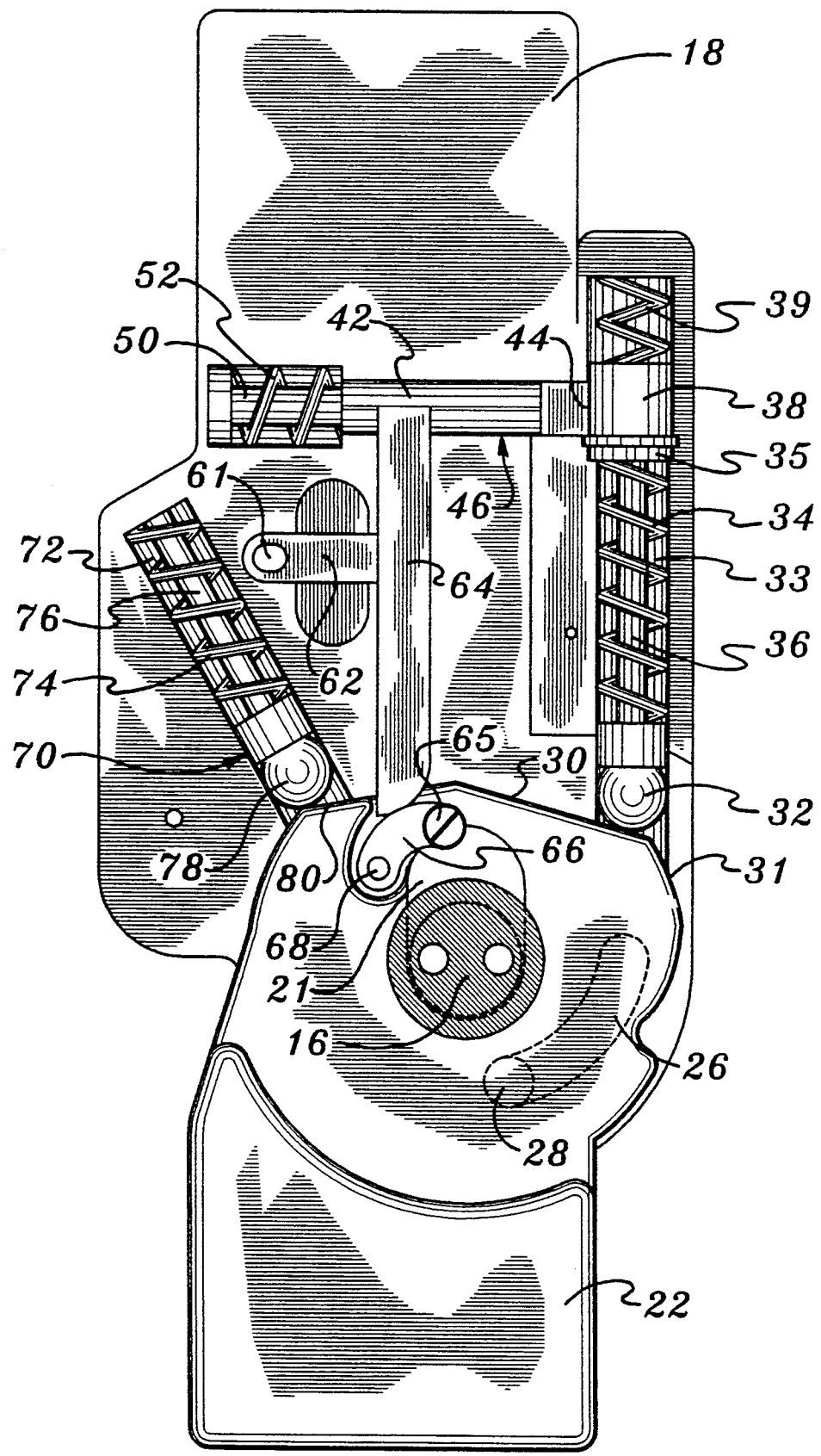
FIG. 4 is a disassembly view as viewed along line 4—4 of FIG. 3.
Figure 5:
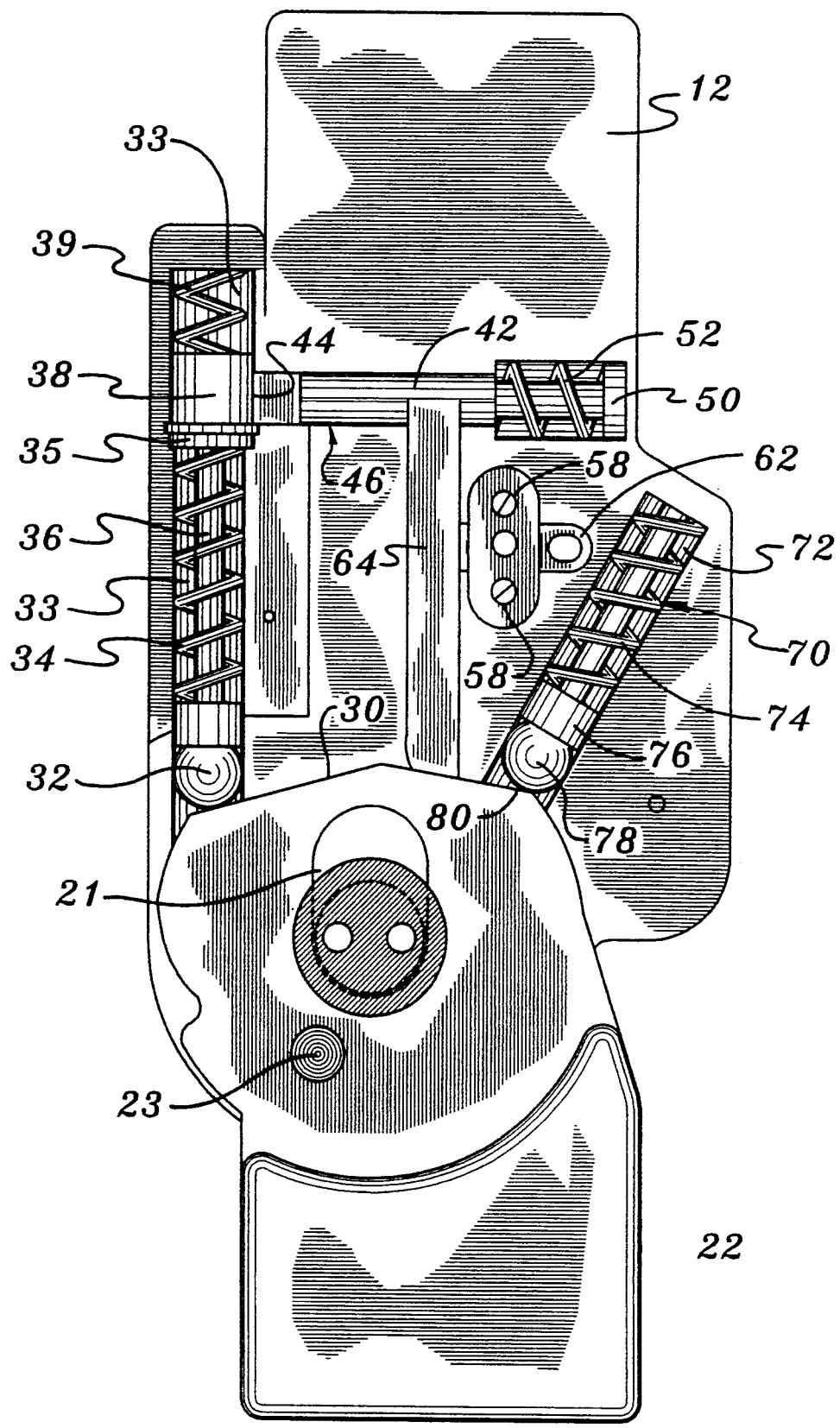
FIG. 5 is a disassembly view as viewed along line 5—5 of FIG. 3.
Figure 6:
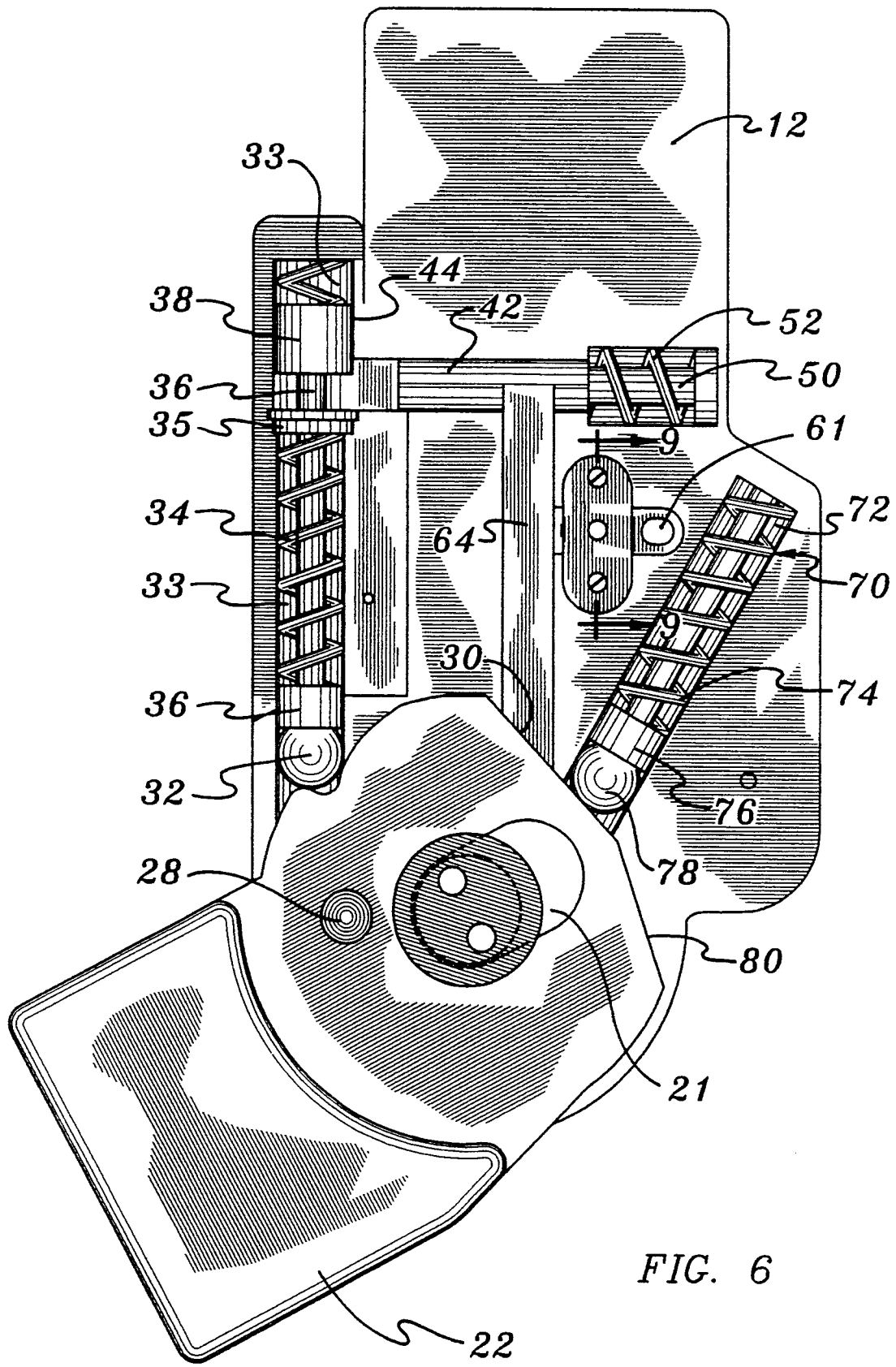
FIG. 6 is the disassembly view as shown in FIG. 5 with a component moved.

A means for limiting the knee flexion range of the knee hinge 10 is contained within the hinge casing 20 and will now be described. As shown in FIGS. 4–6, a contact area 30 is substantially straight in shape and is integrally formed along an interiorly located perimeter portion 31 of the hinge arm 22. A contact 32 is positioned within a journal 33 of the hinge casing assembly 20 and is biased toward the contact area 30 by a coil spring 34 which engages both the contact and a guide 35. Connected to the contact 32 is a plunger 36 that passes through the coil spring 34. The plunger 36 further passes through the guide 35 and engages a limiter 38. As the hinge arm 22 pivots upon the pivot pin 16, the contact area 30 engages the contact 32 which forces the plunger 36 to engage the limiter 38, thereby selectively restricting motion of the hinge arm 22 to the limited knee flexion range of approximately 24 degrees.

The limiter 38 is slidably positioned against the guide 35 within the journal 33 by a spring 39 and is supported against the guide 35 by a holding rod 42 that engages an aperture 44 in the limiter. The holding rod 42 may be disengaged from the aperture 44 to allow the limiter 38 to axially traverse the journal away from the guide 35, thereby allowing an unrestricted movement of the plunger 36 and the contact 32 as can be seen in FIG. 6. This in turn will allow the hinge arm 22 to unrestrictedly pivot about the pivot pin 16, thus allowing a user to obtain a substantially full knee flexion range.

To facilitate a release of the holding rod 42 from the limiter 38 which will allow a user to obtain the substantially full knee flexion range, a release assembly 46 may be actuated. The release assembly 46 comprises a further plunger 50 that supports a further coil spring 52 thereon. The plunger 50 is connected in an axially colinear manner to the holding rod 42. The plunger 50, coupled together with the spring 52, is operable to bias the holding rod out of the aperture 44 in the limiter 38 upon actuation of the release assembly 46, so as to allow for an axial motion of the limiter away from the guide 35. A release of the limiter 38 will allow the hinge arm 22 to unrestrictedly pivot about the pivot pin 16, thereby providing a user with the substantially full knee flexion range.

The release assembly 46 may be selectively actuated by a button 53 which is disposed within a sleeve 54 on an exterior surface 55 of the left member 12. The button 53 is connected to a pair of push rods 56, 57 by two fasteners 58, wherein actuation of the button against a force of a spring 59 will cause the pair of push rods to advance a catch 60 orthogonally away from an aperture 61 in a release 62 as can best be seen in FIG. 9. The release 62 is in mechanical communication with the holding rod 42 and, upon its disengagement from the catch 60 by an actuation of the button 53, the release and the holding rod 42 will move in such a manner so as to allow the holding rod to be removed from the aperture 44 of the limiter 38.

The holding rod 42 may be selectively re-engaged to the aperture 44 of the limiter 38 so as to allow a user to return the knee hinge 10 to the limited knee flexion range. Orthogonally connected to the holding rod 42 is a follower 64 that will push the holding rod into the aperture 44 of the limiter 38 when a cam 65 contacts it. The cam 65 is mounted to the hinge arm 22 and will contact the follower 64 when the hinge arm is positioned in a substantially bent position with respect to the hinge casing assembly 20. As the hinge arm 22 is moved from a bent position to a substantially straight position with respect to the hinge casing assembly 20, the cam 65 will move the follower 64 in such a manner as to cause the associated holding rod 42 to engage the limiter 38. The cam 65 in mounted to the hinge arm 22 by a cam support 66 that pivots upon a cam pivot 68. FIGS. 7 and 8 detail the interaction of the cam 65 against the follower 64 and a respective motion of the holding rod 42 into the aperture 44 of the limiter 38. The cam 65 and the follower 64 provide a user with an automatic resetting of the limited knee flexion range of approximately 24 degrees whenever a user's knee is straightened from a bent position.

The coil spring 34 that biases the contact 32 into engagement with the contact area 30 also has an additional use. The coil spring 34 and its respective plunger 36 and contact 32 provide a force to the hinge arm 22 that substantially straightens the hinge arm, thereby assisting the user in a straightening of the user's knee during a leg movement. The coil spring 34 is of a conventional shape and may be of any desirable stiffness to provide for a variation in an amount of assistance provided to the user. A stiffer coil spring 34 will increase the amount of assistance afforded to any particular user to compensate for weak or damaged knee muscles.

In addition, a spring assist mechanism 70, which performs a substantially oppositely similar function as that of the coil spring 34 discussed above, is disposed within a further journal 72 inside of the hinge casing assembly 20. The spring assist mechanism 70 comprises an even further coil spring 74 disposed upon an even further plunger 76 with a further contact 78 mounted thereto. The coil spring 74 is operable to bias the contact 78 into engagement with a further contact area 80 of the hinge arm 22 so as to cause the hinge arm to assume a substantially bent position with respect to the hinge casing assembly 20. The stiffness of the coil spring 74 may be chosen to selectively increase or decrease the amount of assistance provided to the user. Alternatively, the spring assist mechanism 70 may be selectively removed from the hinge casing assembly to provide no additional assistance to the user.

As to the manner of usage and operation of the present invention, the same should be apparent from the above description. Accordingly, no further discussion relating to the manner of usage and operation will be provided.

In summary, the knee hinge with selectively limited motion optionally limits an available flexion range of a user's knee to approximately 24 degrees so that a user will not fall should the user buckle at the knee. The limited knee flexion range may also be released by pressing a button to provide for a greater range of knee flexion which will allow a user to sit down in a conventional manner. The approximately 24 degree limit of the flexion range is automatically re-engaged whenever the user's knee is straightened. The hinge further provides both a substantially J-shaped motion that follows a user's natural knee motion and a spring mechanism for assisting weak knee muscles. The hinge also allows a small degree of knee hyperextension for the purpose of allowing the user to assume and maintain a safe standing position.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by LETTERS PATENT of the United States is as follows:

1. A new knee brace hinge with selectively limited motion comprising:

a first member and a hinge arm member pivotally connected together by a pin, a journal formed in said first member, a projection secured to said hinge arm member, said projection engaging said journal and permitting said hinge arm member both to slide relative to said first member and to simultaneously pivot relative to said first member about said pin;

a limiting means for selectively limiting a pivotal movement of said hinge arm member relative to said first member, said limiting means comprising a contact movably secured to said first member, said contact being operable to engage a portion of said hinge arm member, thereby limiting said pivotal movement of said hinge arm member to a predetermined degree relative to said first member; a plunger slidably mounted to said first member, said plunger being in mechanical communication with said contact; and a catch operable to engage and secure said plunger in a predetermined position, thereby securing said contact in a further predetermined position;

an operating means for selectively operating said limiting means, said operating means comprising a button in mechanical communication with said catch, said button being operable by a user to selectively disengage said catch from said plunger; and, a reset means to engage said catch to said plunger, said reset means comprising a cam pivotally mounted to said hinge arm member, said cam being operable to selectively operate said catch, thereby to cause said catch to engage said plunger during a predetermined leg movement.

2. The new knee brace hinge with selectively limited motion of claim 1, and further comprising a spring secured to said hinge to bias said hinge arm member into a substantially straight position relative to said first member.

3. The new knee brace hinge with selectively limited motion of claim 2, and further comprising a spring secured to said hinge whereby said spring is operable to selectively bias said hinge arm member into a substantially bent position relative to said first member.

4. The new knee brace hinge with selectively limited motion of claim 3, and further comprising a further spring selectively secured to said hinge to bias said hinge arm member into a substantially straight position relative to said first member.

* * * * *